(12) United States Patent
Hollaender et al.

(10) Patent No.: US 10,670,575 B2
(45) Date of Patent: Jun. 2, 2020

(54) MULTIPHASE FLOW METERS AND RELATED METHODS HAVING ASYMMETRICAL FLOW THERETHROUGH

(71) Applicant: Schlumberger Technology Corporation, Sugar Land, TX (US)

(72) Inventors: Florian Hollaender, Abu Dhabi (AE); Alexander Tuborg Vilstrup, Singapore (SG); Muhammad Fuad Mohamed Zain, Singapore (SG); Guillaume Jolivet, Singapore (SG)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 280 days.

(21) Appl. No.: 15/468,293

(22) Filed: Mar. 24, 2017

(65) Prior Publication Data

US 2018/0274730 A1   Sep. 27, 2018

(51) Int. Cl.
*G01N 33/28* (2006.01)
*F17D 3/01* (2006.01)
*G01F 1/74* (2006.01)
*F17D 1/00* (2006.01)

(52) U.S. Cl.
CPC ......... *G01N 33/2847* (2013.01); *F17D 1/005* (2013.01); *F17D 3/01* (2013.01); *G01F 1/74* (2013.01); *G01N 33/2841* (2013.01)

(58) Field of Classification Search
CPC .. G01F 1/74; G01N 33/2841; G01N 33/2847; F17D 1/005; F17D 3/01
See application file for complete search history.

(56) References Cited

U.S. PATENT DOCUMENTS

| 4,091,835 A | 5/1978 | Frampton |
| 4,144,754 A | 3/1979 | Pitts, Jr. et al. |

(Continued)

FOREIGN PATENT DOCUMENTS

| CN | 203216545 | 9/2013 |
| DE | 9218091 | 7/1993 |

(Continued)

OTHER PUBLICATIONS

International Preliminary Report on Patentabilitly issued in the related PCT application PCT/US2016/041036 dated Jan. 9, 2018 (10 pages).

(Continued)

*Primary Examiner* — Paul M. West
(74) *Attorney, Agent, or Firm* — Cameron R. Sneddon

(57) ABSTRACT

Multiphase flowmeters and related methods having asymmetrical flow therethrough are disclosed. An example method includes configuring an inlet manifold, a first flowline, and a second flowline to decrease a gas fraction in a first fluid flow through the first flowline and increase a gas fraction in a second fluid flow through the second flow line; flowing the first fluid flow through the first flowline and flowing the second fluid flow through the second flow line; and determining at least one of 1) a first water liquid ratio of the first fluid flow through the first flowline; 2) a first liquid flow rate of the first fluid flow through the first flow line; or 3) a first gas flow rate of the first fluid flow through the first flow line.

15 Claims, 9 Drawing Sheets

(56) References Cited

U.S. PATENT DOCUMENTS

| | | | |
|---|---|---|---|
| 4,760,742 A * | 8/1988 | Hatton | F17D 1/005 73/200 |
| 5,390,547 A | 2/1995 | Liu | |
| 5,589,642 A | 12/1996 | Agar et al. | |
| 5,741,977 A | 4/1998 | Agar et al. | |
| 6,532,826 B1 | 3/2003 | Dou | |
| 7,654,151 B2 | 2/2010 | Agar et al. | |
| 7,661,302 B2 | 2/2010 | Gysling | |
| 7,717,000 B2 | 5/2010 | Xie et al. | |
| 7,908,930 B2 | 3/2011 | Xie et al. | |
| 7,942,065 B2 | 5/2011 | Xie | |
| 8,536,883 B2 | 9/2013 | Xie et al. | |
| 8,606,531 B2 | 12/2013 | Pinguet et al. | |
| 8,641,813 B2 | 2/2014 | Gysling | |
| 8,915,145 B1 | 12/2014 | Van Orsdol | |
| 2005/0241410 A1 | 11/2005 | Wium | |
| 2009/0000389 A1 | 1/2009 | Redon | |
| 2010/0145634 A1 | 6/2010 | Pinguet et al. | |
| 2010/0198531 A1 | 8/2010 | Bell et al. | |
| 2010/0305880 A1 | 12/2010 | Oddie | |
| 2011/0283809 A1 | 11/2011 | Pihlaja et al. | |
| 2012/0000643 A1 | 1/2012 | Bruun et al. | |
| 2012/0017697 A1 | 1/2012 | Benzo et al. | |
| 2012/0242081 A1 | 9/2012 | Keays et al. | |
| 2012/0325751 A1 | 12/2012 | Renick et al. | |
| 2013/0206420 A1 | 8/2013 | McHugh et al. | |
| 2013/0327154 A1 | 12/2013 | Xie et al. | |
| 2014/0007696 A1 | 1/2014 | Al-Hadhrami et al. | |
| 2014/0041463 A1 | 2/2014 | Vethe et al. | |
| 2014/0137643 A1 | 5/2014 | Henry et al. | |
| 2014/0331783 A1 | 11/2014 | Xie | |
| 2015/0185062 A1 | 7/2015 | Ahmad et al. | |
| 2017/0010139 A1 | 1/2017 | Vilstrup et al. | |
| 2018/0010944 A1 | 1/2018 | Xie et al. | |
| 2018/0143052 A1 | 5/2018 | Xie et al. | |

FOREIGN PATENT DOCUMENTS

| | | |
|---|---|---|
| EP | 1744131 A1 | 1/2007 |
| EP | 2171407 A1 | 4/2010 |
| WO | WO2002088519 A1 | 11/2002 |

OTHER PUBLICATIONS

Office Action issued in the related RU Application 2018104459 dated Sep. 20, 2018 (14 pages).

European Search Report issued in the related EP Application 168218901.7 dated Nov. 7, 2018 (3 pages).

Office Action issued in the related EP Application 16821890.7 dated Nov. 19, 2018 (3 pages).

International Search Report and Written Opinion issued in the related PCT application PCT/US2016/030165 dated Aug. 4, 2016 (13 pages).

Office Action issued in the related RU application 2017141565 dated Jun. 20, 2018 (12 pages).

Office Action issued in the related CN application 201680039205.8 dated Nov. 23, 2018 (13 pages).

Decision of Grant issued in the related RU application 2017141565 dated Nov. 30, 2018 (18 pages).

International Search Report and Written Opinion issued in the related PCT application PCT/US2016/041036 dated Nov. 1, 2016 (14 pages).

International Search Report and Written Opinion issued in the related PCT application PCT/US2018/023447 dated Jul. 9, 2018 (15 pages).

Office action issued in the related U.S. Appl. No. 15/973,133 dated Jul. 30, 2018 (16 pages).

Office Action issued in the related U.S. Appl. No. 15/204,207 dated Aug. 2, 2018 (23 pages).

Office Action issued in the related U.S. Appl. No. 15/570,497 dated Apr. 18, 2019, 35 pages.

Second Office Action Received in Chinese Patent Application No. 2016080039205.8 dated Sep. 12, 2019, 9 pages with English Summary.

International Preliminary Report on Patentability issued in the related PCT application PCT/US2018/023447 dated Oct. 3, 2019 (14 pages).

* cited by examiner

|  | SINGLE METER | EVEN SPLIT | | UNEVEN SPLIT | |
|---|---|---|---|---|---|
|  |  | METER 1 | METER 2 | METER 1 | METER 2 |
| GAS RATE (m³/hr) | 200 | 100 | 100 | 66.7 | 133.3 |
| LIQUID RATE (m3/hr) | 15 | 7.5 | 7.5 | 12 | 3 |
| GVF (%) | 93.0% | 93.0% | 93.0% | 84.7% | 97.8% |
| PORTION OF GAS | 1 | 0.5 | 0.5 | 0.33 | 0.67 |
| PORTION OF LIQUID | 1 | 0.5 | 0.5 | 0.8 | 0.2 |
| GAS UNCERTAINTY (% REL) | 7% | 7% | 7% | 8% | 4% |
| LIQUID UNCERTAINTY (% REL) | 5% | 5% | 5% | 2.5% | 10% |
| WLR UNCERTAINTY (% ABS) | 5% | 5% | 5% | 2% | 8% |
| COMBINED GAS UNCERTAINTY | 7% | 4.9% | | 3.8% | |
| COMBINED LIQUID UNCERTAINTY | 5% | 3.5% | | 2.8% | |
| COMBINED WLR UNCERTAINTY | 5% | 3.5% | | 2.3% | |

FIG. 9

MULTIPHASE FLOW METERS AND RELATED METHODS HAVING ASYMMETRICAL FLOW THERETHROUGH

FIELD OF THE DISCLOSURE

This disclosure relates generally to hydrocarbon production and, more particularly, to multiphase flowmeters and related methods having asymmetrical flow therethrough.

DESCRIPTION OF RELATED ART

Hydrocarbons are widely used as a primary source of energy and have a great impact on the world economy. Consequently, the discovery and efficient production of hydrocarbon resources is increasingly important. As relatively accessible hydrocarbon deposits are depleted, hydrocarbon prospecting and production has expanded to new regions that may be more difficult to reach and/or may pose new technological challenges. During typical operations, a borehole is drilled into the earth, whether on land or below the sea, to reach a reservoir containing hydrocarbons. Such hydrocarbons are typically in the form of oil, gas, or mixtures thereof that may be brought to the surface through the borehole.

SUMMARY

An example method includes configuring an inlet manifold, a first flowline, and a second flowline to decrease a gas fraction in a first fluid flow through the first flowline and increase a gas fraction in a second fluid flow through the second flow line; flowing the first fluid flow through the first flowline and flowing the second fluid flow through the second flow line; and determining at least one of 1) a first water liquid ratio of the first fluid flow through the first flowline; 2) a first liquid flow rate of the first fluid flow through the first flow line; or 3) a first gas flow rate of the first fluid flow through the first flow line.

An example method includes flowing fluid into an inlet manifold; and diverting the fluid based on a configuration of the inlet manifold between a first fluid flow through a first flowline and a second fluid flow through a second flow line, the first fluid flow having a first phase fraction different than a second phase fraction of the fluid second flow.

An example apparatus includes an inlet manifold; an outlet; and first and second flowlines coupled between the inlet manifold and the outlet, when the inlet manifold receives a multiphase fluid, the inlet manifold causes the flow of a first multiphase fluid having a first gas fraction through the first flowline and causes the flow of a second multiphase fluid having a second gas fraction through the second flowline, the first gas fraction is less than the second gas fraction.

BRIEF DESCRIPTION OF THE DRAWINGS

FIG. 9 illustrates results obtained in accordance with the teachings of this disclosure.

The figures are not to scale. Wherever possible, the same reference numbers will be used throughout the drawing(s) and accompanying written description to refer to the same or like parts.

DETAILED DESCRIPTION

Figure 1:
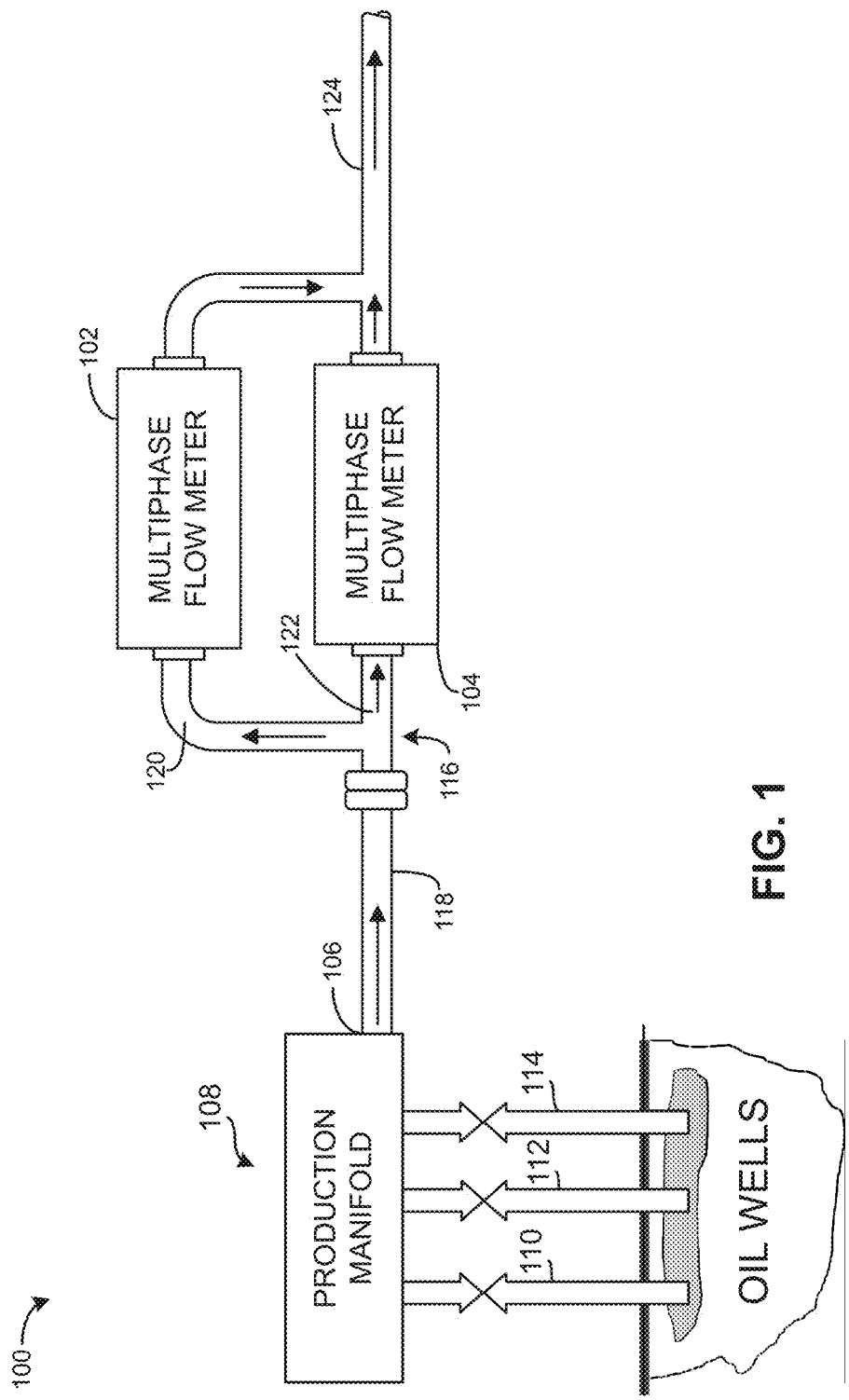
FIG. 1 illustrates a side view of example multiphase flow meters coupled to a wellhead in a first asymmetrical flowline arrangement.

The examples disclosed herein relate to improving the accuracy of measurements obtained from multiphase flowmeters. In some examples, the measurements are used to determine the liquid flow rate, the gas flow rate, and/or the water liquid ratio of the fluid flowing through flowlines associated with the respective multiphase flowmeters. In other words, the examples disclosed herein relate to enabling asymmetrical phase fractions having a lower combined gas uncertainty (e.g., less error), a lower combined liquid uncertainty (e.g., less error), and/or a lower combined water liquid ratio uncertainty (e.g., less error).

In some examples, to enable characteristics of the fluid to be determined while accommodating different oil and gas production flow rates, an inlet manifold may divert fluid between first and second flow paths such that the fluid flowing through the first flow path has the same or substantially the same gas fraction, oil fraction, and water fraction as the fluid flowing through the second flow path. In some examples, the characteristics mentioned may be used to determine the water liquid ratio and liquid and gas flow rates of the fluid flowing through the first and second flow paths. In examples in which the gas fraction of the fluid is relatively high, the accuracy of the determined water liquid ratio (WLR) and the determined liquid rate may be low. Thus, in examples in which the gas fraction of the fluid in both the first and second flow paths is relatively high, the accuracy of the determined WLR and liquid rate for both flow paths may be relatively low. As used herein, substantially the same gas fraction, oil fraction, and water fraction means where there is no purposeful separation of the multiphase fluid at the inlet manifold to cause, enable and/or encourage the multiphase fluid flowing through the first flow path to have a higher gas fraction than the multiphase fluid flowing through the second flow path.

In other examples, to enable characteristics of the fluid to be determined while accommodating different oil and gas production flow rates, an example inlet manifold and/or flow junction may divert multiphase fluids between first and second flow paths such that the multiphase fluid flowing through the first flow path has a first gas fraction and a first liquid fraction and the multiphase fluid flowing through the second flow path has a second gas fraction and a second liquid fraction where the first gas fraction is less than the second gas fraction and the first liquid fraction is greater than the second liquid fraction. To enable the multiphase fluid to be diverted between the first and second flow paths, the example inlet manifold is configured to have at least two branches or flow paths that enable momentum and gravity to urge liquid-rich fluid through a first flow path and to urge gas-rich fluid through a second flow path. Specifically, the inlet manifold configuration orients the first flow path to be coaxial with an inlet of the inlet manifold and the second flow path to be non-coaxial with the inlet of the inlet manifold. Further, the second flow path may be vertically displaced to be at a higher elevation than the first flow path. In this manner, the momentum and weight of the liquid component of the multiphase fluid relative to the gas component flowing into the inlet manifold tends to cause more of the liquid component to follow the first flow path than the second flow path. Thus, in contrast to examples in which the fluid fraction through the first and second flow paths are substantially the same, the examples disclosed herein enable multiphase fluids to be diverted between first and second flowlines to stimulate, cause, prompt, induce, foster, enable and/or encourage the first flowline to have a lesser gas fraction than the second flowline to enable a multiphase flow meter coupled to the first flowline to determine WLR and liquid rate with increased accuracy. In other words, the examples disclosed herein purposefully configure and/or design flowlines to achieve a gas-rich flow in one of the flowlines and a liquid-rich flow in another of the flowlines.

FIG. 1 illustrates an example wellsite 100 including an example first multiphase flow meter 102 and an example second multiphase flow meter 104 coupled in an arrangement to enable asymmetrical flow in accordance with the teachings of this disclosure. While FIG. 1 depicts one example of enabling asymmetrical flow, other examples may be employed in accordance with the teachings of this disclosure to enable asymmetrical flow. In the illustrated example, the first and second multiphase flowmeters 102, 104 are permanently coupled to an outlet 106 of a production manifold 108, which is coupled to a wellhead of a first oil well 110, a wellhead of a second oil well 112 and a wellhead of a third oil well 114.

In this example, to divert a first multiphase fluid having a first phase fraction to the first multiphase flowmeter 102 and to divert second multiphase fluid having a second phase fraction to the second multiphase flowmeter 104, an example inlet manifold 116 is coupled between a flowline 118 and the first and second multiphase flowmeters 102, 104 where the flowline 118 is directly coupled to the production manifold 108. In the illustrated example, the inlet manifold 116 does not include a separator. In the illustrated example, the inlet manifold 116 includes a first branch or portion 120 and a second branch or portion 122 where the second portion 122 is substantially coaxial with the flowline 118 and the first portion 120 is offset and/or non-coaxial with the flowline 118. Further, as illustrated in FIG. 1, the first portion 120 of the inlet manifold 116 is vertically offset from the second portion 122 to enable the first portion 120 to be at a higher elevation than the second portion 122. As used herein, substantially coaxial accounts for assembly tolerances in an oil field environment.

In operation, multiphase fluid flows from the production manifold 108 through the flowline 118 to the inlet manifold 116. In some examples, the inlet manifold 116 encourages and/or enables a gas-rich fluid to flow through the first portion 120 and a liquid-rich fluid to flow through the second portion 122. For example, the inlet manifold 116 encourages and/or enables the gas-rich fluid to flow through the first portion 120 to the first multiphase flow meter 102 based on the first portion 120 being offset (e.g., vertically) relative to the longitudinal axis of the flowline 118. Specifically, gravity and momentum encourage (e.g., gas tends to rise and the liquid component will have a greater momentum than the gas component) a liquid-rich fluid to flow through the second portion 122 as a result of the substantially coaxial positioning of the second portion 122 relative to the flowline 118 and/or the vertical displacement of the first portion 120 of the manifold 116 relative to the second portion 122. In some examples, to encourage the liquid-rich fluid to flow through the second portion 122 and to encourage the gas-rich fluid to flow through the first portion 120, the inlet manifold 116 includes an intrusive element such as, for example, a helical insert, a flow straightener, an elbow, etc. The flow straightener may split the flow into multiple straight flow paths and/or vanes that encourage gravity separation. However, in other examples, the inlet manifold 116 does not include such an intrusive element.

As the first multiphase fluid flows through the first multiphase flowmeter 102, in some examples, the first multiphase flowmeter 102 determines characteristics of the multiphase fluid such as, for example, a first gas flow rate, a first liquid flow rate and a first water liquid ratio (WLR). As the second multiphase fluid flows through the second multiphase flowmeter 104, in some examples, the second multiphase flowmeter 104 determines characteristics of the multiphase fluid such as, for example, a second gas flow rate, a second liquid flow rate and a second WLR. After the multiphase fluid flows through the respective first and second multiphase flowmeters 102, 104, the flows are combined at an exit and/or exit manifold 124.

In some examples, Equation 1 is used to determine total gas flow rates through the first and second multiphase flowmeters 102, 104 where $q_{gas\_Total}$ represents the total gas flow rate through the first and second multiphase flowmeters 102, 104, $q_{gas\_1}$ represents the gas flow rate through the first multiphase flowmeter 102 and $q_{gas\_2}$ represents the gas flow rate through the second multiphase flowmeter 104.

$$q_{gas\_Total} = q_{gas\_1} + q_{gas\_2} \quad (1)$$

In some examples, Equation 2 is used to determine total liquid flow rates through the first and second multiphase flowmeters 102, 104 where $q_{liq\_Total}$ represents the total liquid flow rate through the first and second multiphase flowmeters 102, 104, $q_{liq\_1}$ represents the gas flow rate through the first multiphase flowmeter 102 and $q_{liq\_2}$ represents the gas flow rate through the second multiphase flowmeter 104.

$$q_{liq\_Total} = q_{liq\_1} + q_{liq\_2} \quad (2)$$

In some examples, Equation 3 is used to determine the total water liquid ratio through the first and second multiphase flowmeters 102, 104 where $WLR_{Total}$ represents the total water liquid ratio through the first and second multiphase flowmeters 102, 104, $WLR_1$ represents the water liquid ratio through the first multiphase flowmeter 102 and $WLR_2$ represents the water liquid ratio through the second multiphase flowmeter 104.

$$WLR_{Total} = \frac{WLR_1 q_{liq\_1} + WLR_2 q_{liq\_2}}{q_{liq\_1} + q_{liq\_2}} \quad (3)$$

Equation 4 can be used to express the standard deviation and/or uncertainty of the total gas fraction measurement where σ represents the standard deviation and/or uncertainty of the first and/or second multiphase fluid meters 102, 104, σq$_{gas\_Total}$ represents the standard deviation and/or uncertainty applied to the total gas rate, σq$_{gas\_1}$ represents the standard deviation and/or uncertainty applied to the first gas rate from the first multiphase flowmeter 102 and act σq$_{gas\_2}$ represents the standard deviation and/or uncertainty applied to the second gas rate from the second multiphase flowmeter 104.

$$(\sigma q_{gas\_Total})^2 = (\sigma q_{gas\_1})^2 + (\sigma q_{gas\_2})^2 \qquad (4)$$

Equation 4 can be rewritten as Equation 5.

$$(\sigma q_{gas\_Total})^2 = (q_{gas\_1})^2 \left(\frac{\sigma q_{gas\_1}}{q_{gas\_1}}\right)^2 + (q_{gas\_2})^2 \left(\frac{\sigma q_{gas\_2}}{q_{gas\_2}}\right)^2 \qquad (5)$$

If $x_1$ is defined as the fraction of total gas flowing through the first multiphase flowmeter 102 (i.e., $q_{gas\_1} = x_1 q_{gas\_Total}$), Equation 5 can be written as Equation 6.

$$\left(\frac{\sigma q_{gas\_Total}}{q_{gas\_Total}}\right)^2 = x_1^2 \left(\frac{\sigma q_{gas\_1}}{q_{gas\_1}}\right)^2 + (1-x_1)^2 \left(\frac{\sigma q_{gas\_2}}{q_{gas\_2}}\right)^2 \qquad (6)$$

If $y_1$ is defined as the fraction of the total liquid flowing through the first multiphase flowmeter 102 (i.e., $q_{liquid\_1} = y_1 q_{liquid\_Total}$), Equation 6 can be written for the liquid rate relative uncertainty as Equation 7.

$$\left(\frac{\sigma q_{liquid\_Total}}{q_{liquid\_Total}}\right)^2 = y_1^2 \left(\frac{\sigma q_{liquid\_1}}{q_{liquid\_1}}\right)^2 + (1-y_1)^2 \left(\frac{\sigma q_{liquid\_2}}{q_{liquid\_2}}\right)^2 \qquad (7)$$

Equation 8 is used to determine the total water liquid ratio through the first and second multiphase flowmeters 102, 104 by substituting $x_1$ and $y_1$ into Equation 3.

$$WLR_{Total} = \qquad (8)$$
$$\frac{WLR_1 y_1 q_{liq\_Total} + WLR_2 (1-y_1) q_{liq\_Total}}{q_{liq\_Total}} = WLR_1 y_1 + WLR_2 (1-y_1)$$

Equation 9 can be used to express the standard deviation and/or uncertainty of the water liquid ratio where σWLR$_{Total}$ represents the standard deviation and/or uncertainty applied to the total water liquid ratio, σWLR$_1$ represents the standard deviation and/or uncertainty applied to the first water liquid ratio for the first multiphase flowmeter 102 and σWLR$_2$ represents the standard deviation and/or uncertainty applied to the second water liquid ratio for the second multiphase flowmeter 104.

$$(\sigma WLR_{Total})^2 = y_1^2 (\sigma WLR_1)^2 + (1-y_1)^2 (\sigma WLR_2)^2 \qquad (9)$$

Figure 2:
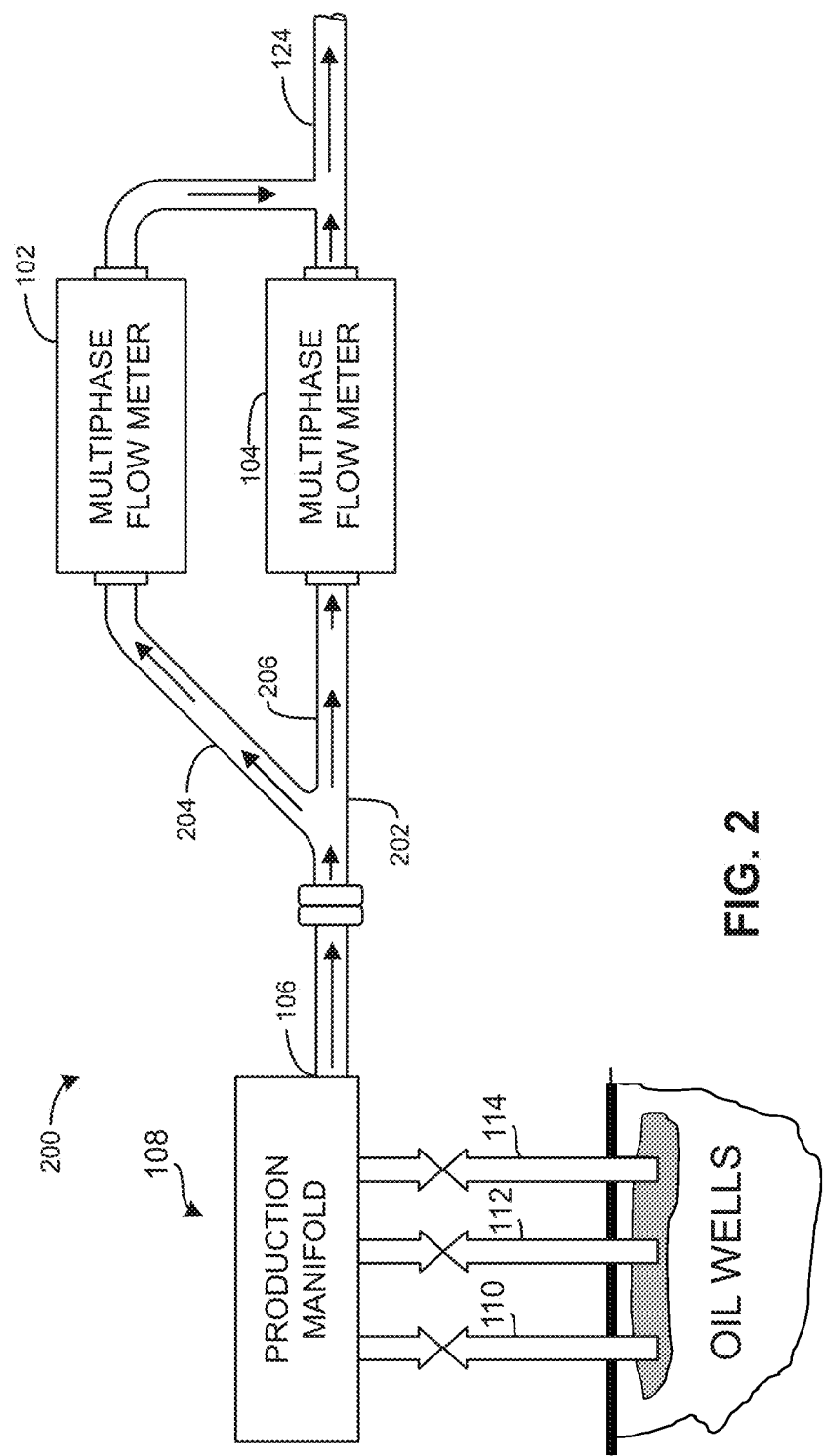
FIG. 2 illustrates a side view of example multiphase flowmeters coupled to a wellhead in a second asymmetrical flowline arrangement.

FIG. 2 illustrates an example wellsite system 200 that is similar to the wellsite system 100 of FIG. 1. However, in contrast to the wellsite system 100 in FIG. 1, the wellsite system 200 of FIG. 2 includes a y-shaped inlet manifold 202 that enables and/or encourages first multiphase fluid having a first phase fraction to be diverted through a first branch or portion 204 of the inlet manifold 202 toward the first multiphase flowmeter 102 and to encourage second multiphase fluid having a second phase fraction to be diverted through a second branch or portion 206 of the inlet manifold 202. In some examples, the y-shaped manifold 202 may encourage less phase separation than the inlet manifold 116 based on the angle between the first and second portions 204, 206 being approximately 45-degrees as opposed to 90-degrees. Of course, other angles between the first and second branches or portions of an inlet manifold can be used to achieve a desired degree of phase separation of a multiphase fluid flow. Namely, the angle can be increased toward 90 degrees to increase the degree of phase separation, or decreased toward, for example, zero degrees to decrease the degree of phase separation.

Figure 3:
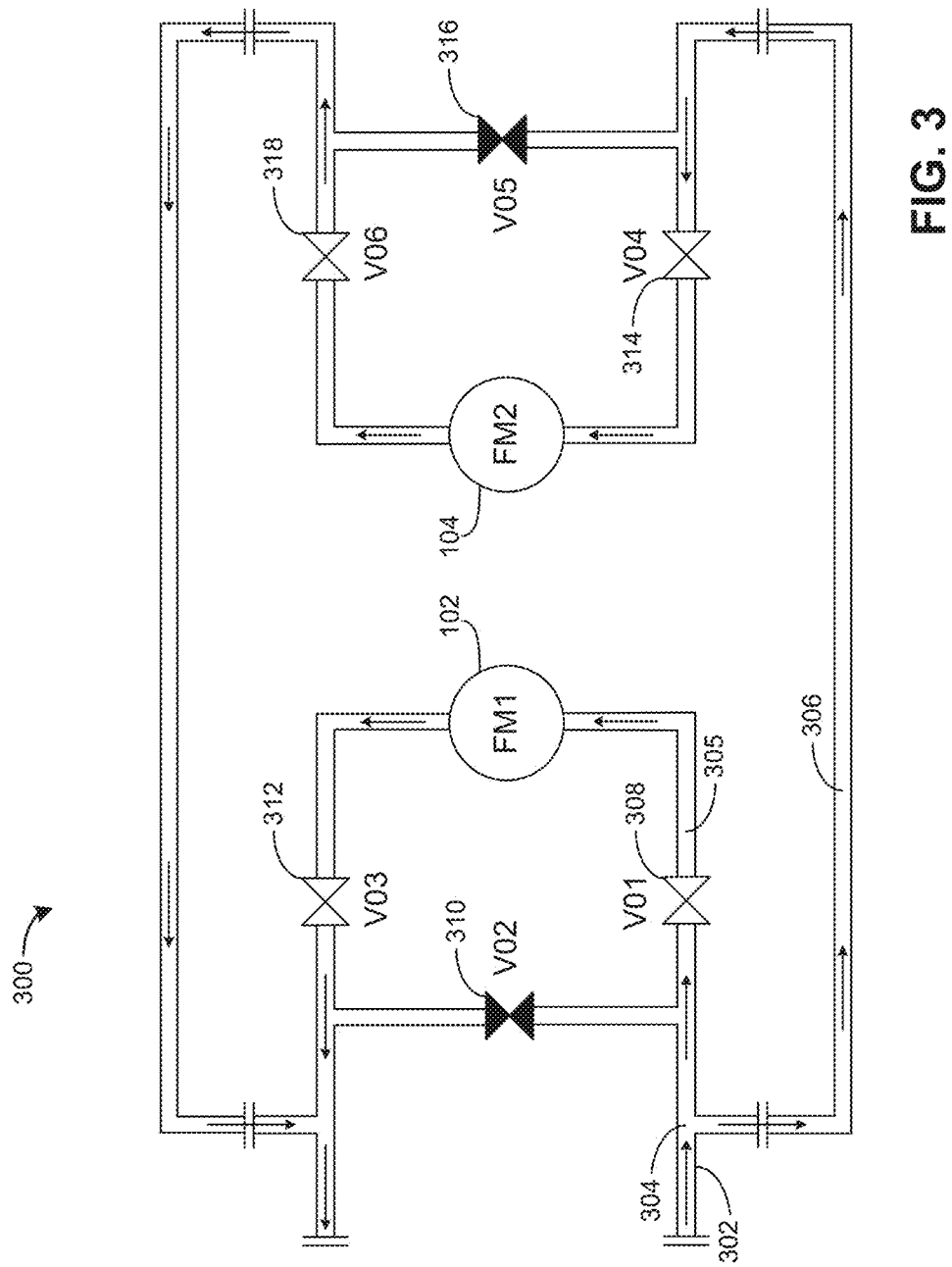
FIG. 3 illustrates a plan view of example multiphase flowmeters coupled in a third asymmetrical flowline arrangement.

FIG. 3 illustrates a plan view of an example apparatus 300 used to divert liquid-rich solutions toward the first multiphase flowmeter 102 and to divert gas-rich solutions toward the second multiphase flowmeter 104. In this example, the apparatus 300 includes an inlet 302 that flows fluid toward an intersection 304 that separates a first flowline 306 and a second flowline 305, where the second flowline 305 flows fluid to the first multiphase flowmeter 102 and the first flowline 306 flows fluid to the second multiphase flow meter 104. In the illustrated example, the apparatus 300 includes a first valve 308, a second valve 310 and a third valve 312 that may be selectively actuated to control fluid flow through the first multiphase flowmeter 102. Similarly, to control fluid flow through the second multiphase flowmeter 104, the apparatus 300 includes a fourth valve 314, a fifth valve 316 and a sixth valve 318 that may be selectively actuated to control fluid flow through the second multiphase flowmeter 104.

In operation, the intersection 304 enables and/or encourages liquid-rich fluid to flow through the second flowline 305 and enables and/or encourages gas-rich fluid to flow through the first flowline 306. Thus, using the example apparatus 300, the multiphase fluid entering the inlet 302 is separated between a liquid-rich fluid that flows through the second flowline 305 and a gas-rich fluid that flows through the first flowline 306 where the liquid-rich fluid includes gas and the gas-rich fluid includes liquid. While some of the examples disclosed herein refer to the gas-rich fluid flowing through the first flowline and liquid-rich fluid flowing through the second flowline, in other examples, the liquid-rich fluid flows through the first flowline and the gas-rich fluid flows through the second flowline.

Figure 4:
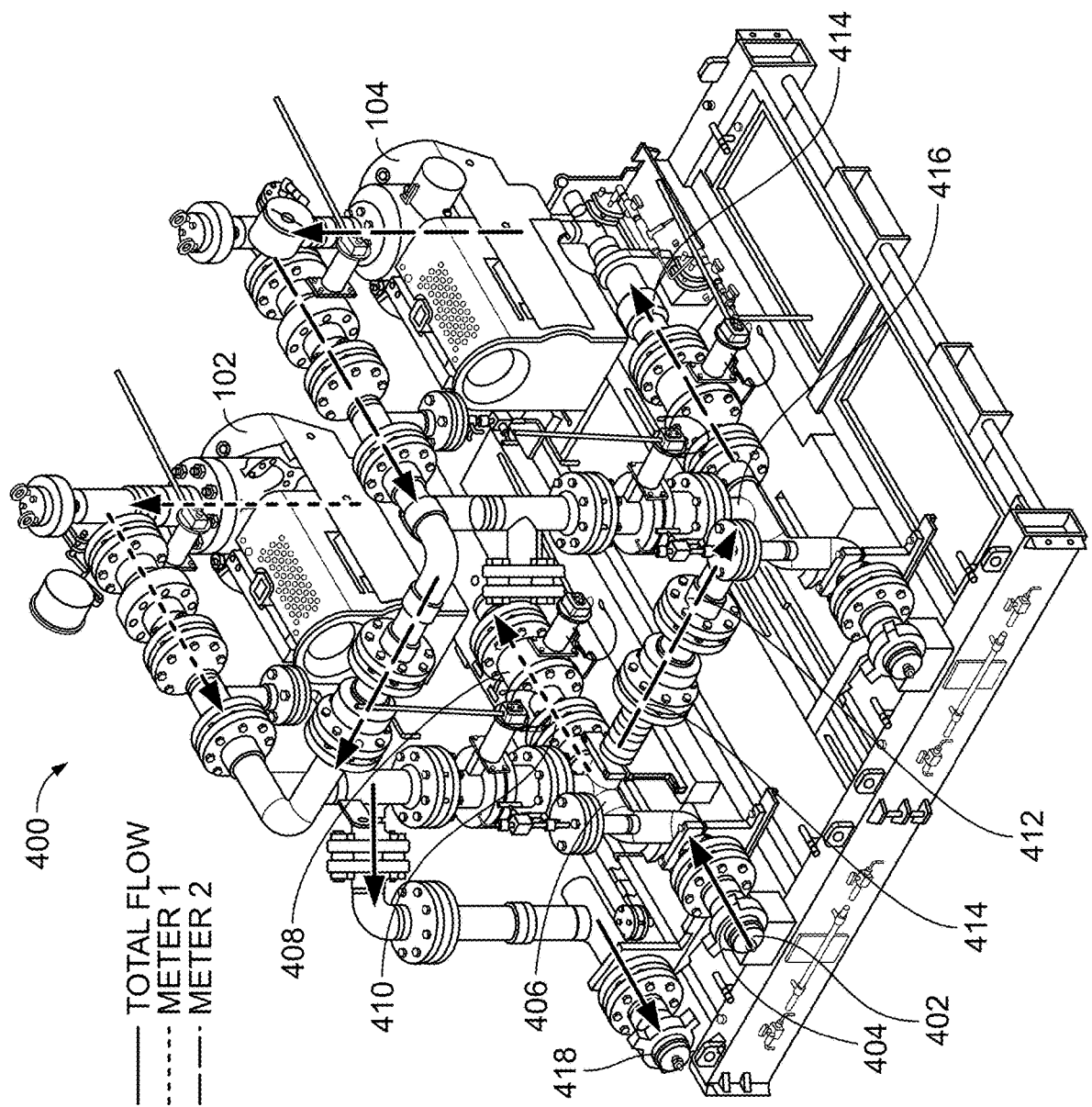
FIG. 4 illustrates an example mobile apparatus including multiphase flowmeters coupled in a fourth asymmetrical flowline arrangement that illustrates fluid being received at a first inlet of the mobile apparatus.

FIG. 4 illustrates an example mobile apparatus 400 including the example first multiphase flowmeter 102 and the example second multiphase flowmeter 104 coupled in an asymmetrical flow arrangement in accordance with the teachings of this disclosure.

In operation, multiphase fluid flows into an inlet 402 in a direction generally indicated by arrow 404 toward a manifold 406 that diverts the flow through a first flowline 408 in a direction generally indicated by arrow 410 and a second flowline 412 in a direction generally indicated by arrow 414. In the illustrated example, the manifold 406 is configured to enable and/or encourage a liquid-rich flow through the first flowline 408 toward the first multiphase flowmeter 102 and to encourage a gas-rich flow through the second flowline 412 and a third flowline 416 toward the second multiphase flowmeter 104. In some examples, the placement or position of the first flowline 408 relative to the second flowline 412 encourages the liquid-rich flow through the first flowline 408 and the gas-rich flow through the second flowline 412. In some examples, the sizing of the first flowline 408 relative to the second flowline 412 encourages the liquid-rich flow through the first flowline 408 and the gas-rich flow through the second flowline 412.

As the multiphase fluid flows through the first multiphase flowmeter 102, the first multiphase flowmeter 102 determines characteristics of the fluid such as, for example, a first gas flow rate, a first liquid flow rate and a first WLR. Similarly, as the multiphase fluid flows through the second multiphase flowmeter 104, the second multiphase flowmeter 104 determines characteristics of the fluid such as, for example, a second gas flow rate, a second liquid flow rate and a second WLR. The first multiphase flowmeter 102 and/or the second multiphase flowmeter 104 may use one or more of Equations 1-9 to determine the total gas flow rates through the first and second multiphase flowmeters 102, 104. Additionally or alternatively, the first multiphase flowmeter 102 and/or the second multiphase flowmeter 104 may use one or more of Equations 1-9 to determine the total liquid flow rates through the first and second multiphase flowmeters 102, 104 and/or the total WLR through the first and second multiphase flowmeters 102, 104. Additionally or alternatively, the first multiphase flowmeter 102 and/or the second multiphase flowmeter 104 may use one or more of Equations 1-9 to determine the standard deviation and/or uncertainty of the first and/or second multiphase flowmeters 102, 104 as applied to the gas flow rate through the apparatus 400 and/or the first and/or second multiphase flowmeters 102, 104, the liquid flow rate through the apparatus 400 and/or first and/or second multiphase flowmeters 102, 104 and/or the WLR of the fluid flowing through the apparatus 400 and/or the first and/or second multiphase flowmeters 102, 104. After the fluid flows through the respective first and second multiphase flowmeters 102, 104, the flows are combined at an exit manifold and/or outlet 418.

Figure 5:
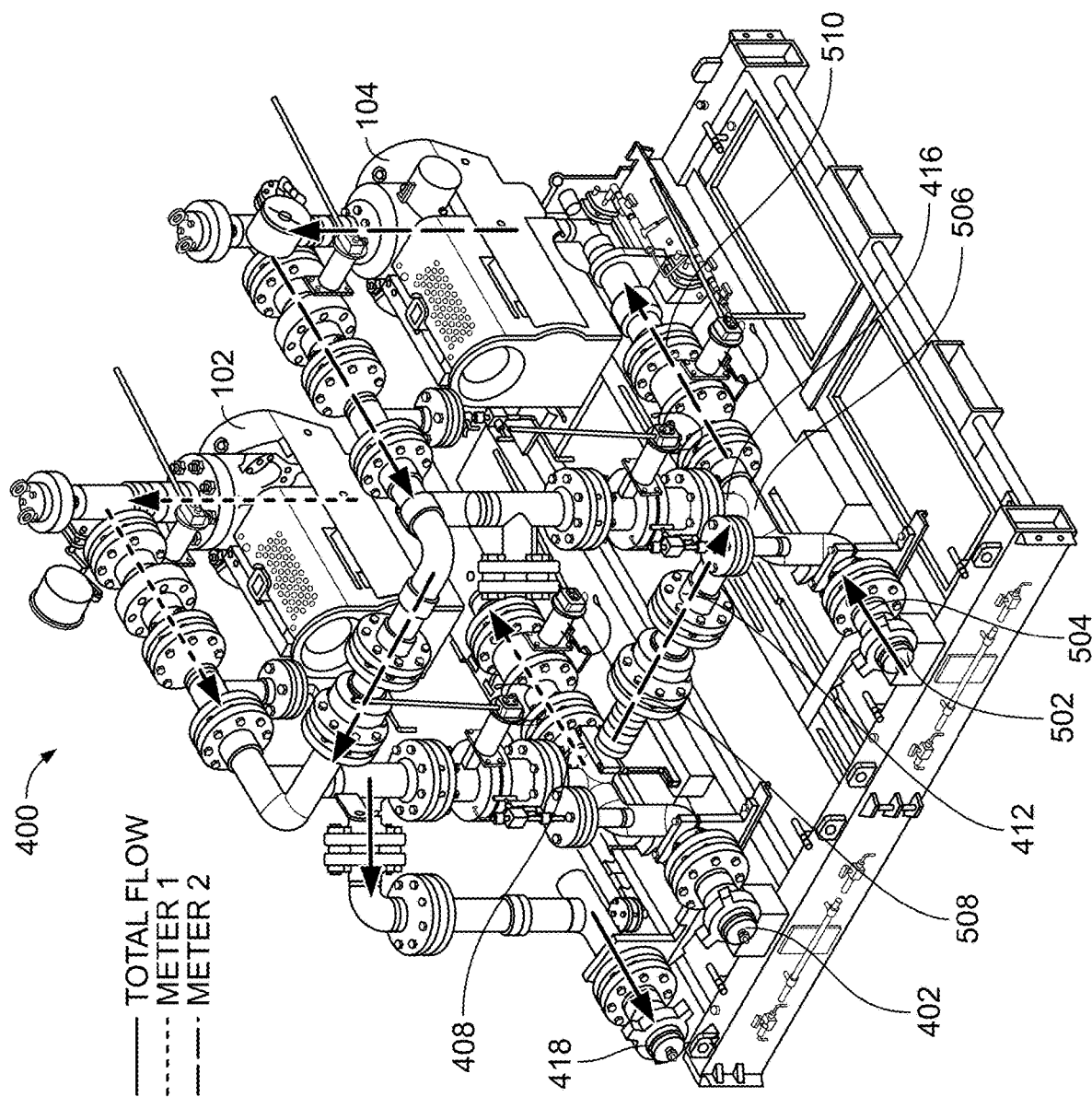
FIG. 5 illustrates the example mobile apparatus of FIG. 4 receiving fluid through a second inlet of the mobile apparatus.

FIG. 5 illustrates an alternative configuration of the example mobile apparatus 400 of FIG. 4. In contrast to the example of FIG. 4, the example of FIG. 5 flows fluid into a second inlet 502 as opposed to the first inlet 402. In operation, based on the multiphase fluid flowing into the inlet 502 in a direction generally indicated by arrow 504, an example manifold 506 separates and/or diverts the multiphase flow between the second flowline 412 in a direction generally indicated by arrow 508 toward the first multiphase flowmeter 102 and the third flowline 416 in a direction generally indicated by arrow 510 toward the second multiphase flow meter 104.

Figure 6:
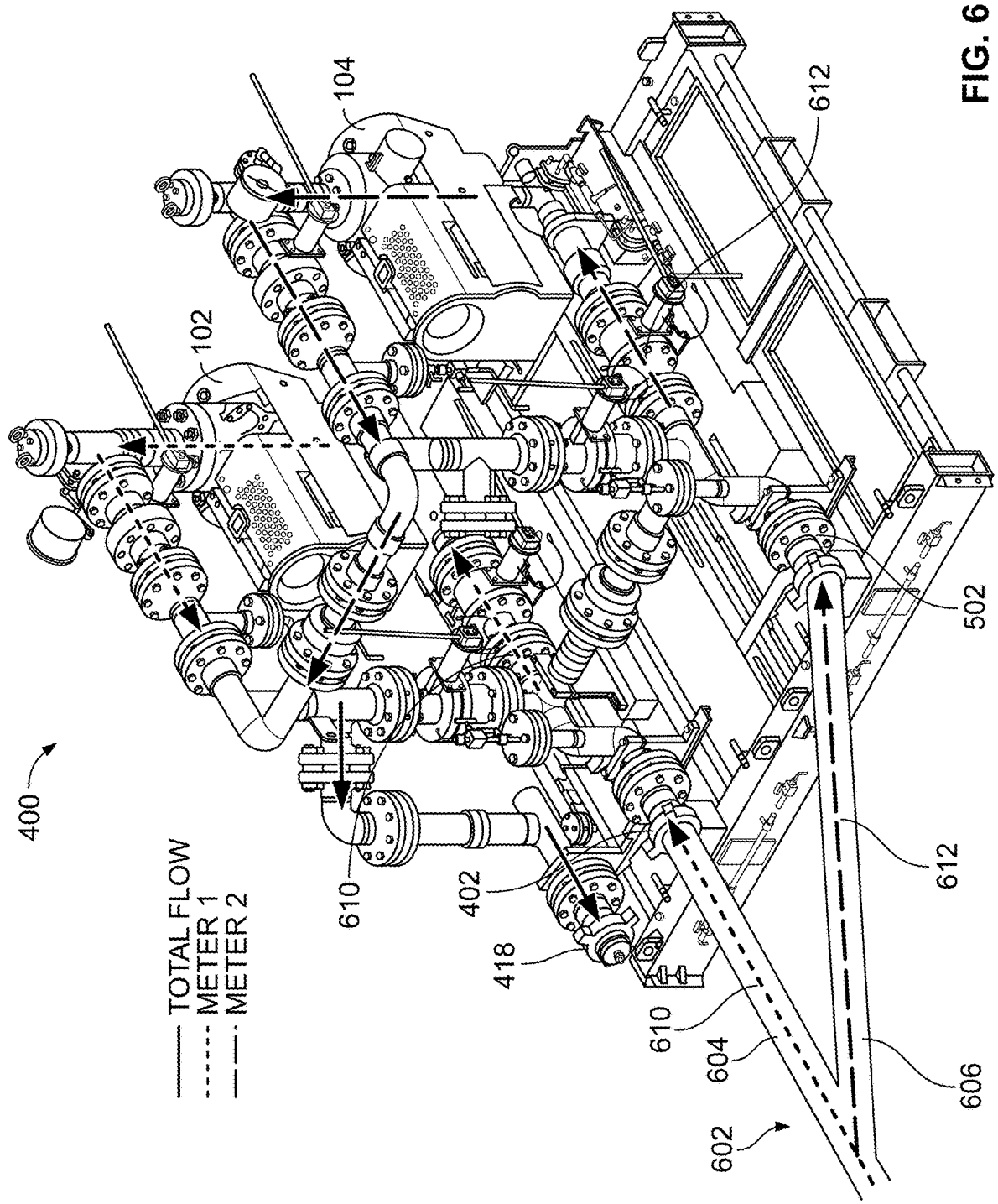
FIG. 6 illustrates the example apparatus of FIG. 4 including an example inlet manifold that flows fluid to the first and second inlets.

FIG. 6 illustrates another alternative configuration of the example mobile apparatus 400 of FIG. 4. In contrast to the examples of FIGS. 4 and 5, the example of FIG. 6 includes an example inlet manifold 602 that diverts the fluid between a first flowline portion 604 and a second flowline portion 606.

In operation, after the fluid is split by the inlet manifold 602, liquid-rich fluid flows into the first inlet 402 in a direction generally indicated by arrow 610 toward the first multiphase flowmeter 102 and gas-rich fluid flows into the second inlet 502 in a direction generally indicated by arrow 612 toward the second multiphase flowmeter 104.

While the examples above disclose flowlines positioned in certain configurations, the examples disclosed herein may be implemented with flowlines in any vertical position (e.g., heights) and/or at any angle relative to one another. For example, the inlet manifold may form an angle between first and second flowlines at approximately 30-degrees, 45-degrees, 90-degrees, 180-degrees and/or any other angle to enable, support and/or encourage the formation of a first fluid stream having a first gas fraction and a first oil fraction and a second fluid stream having a second gas fraction and a second oil fraction where the first gas fraction is greater than the second gas fraction and the first oil fraction is less than the second oil fraction. In some examples, one or more of the flowlines disclosed in accordance with the teachings of this disclosure are disposed vertically (e.g., vertical relative to the earth's surface, non-horizontal relative to the earth's surface), horizontally (e.g., horizontal relative to the earth's surface) and/or at an angle (e.g., a 45-degree angle relative to the earth's surface) to encourage the formation of a first fluid stream having a first gas fraction and a first oil fraction and a second fluid stream having a second gas fraction and a second oil fraction where the first gas fraction is greater than the second gas fraction and the first oil fraction is less than the second oil fraction. Further, while the example inlet manifolds disclosed herein depict two divergent flow paths, inlet manifolds having more than two flow paths may be used if desired to achieve more than two fluid flows having more than two levels of phase separation.

Figure 7:
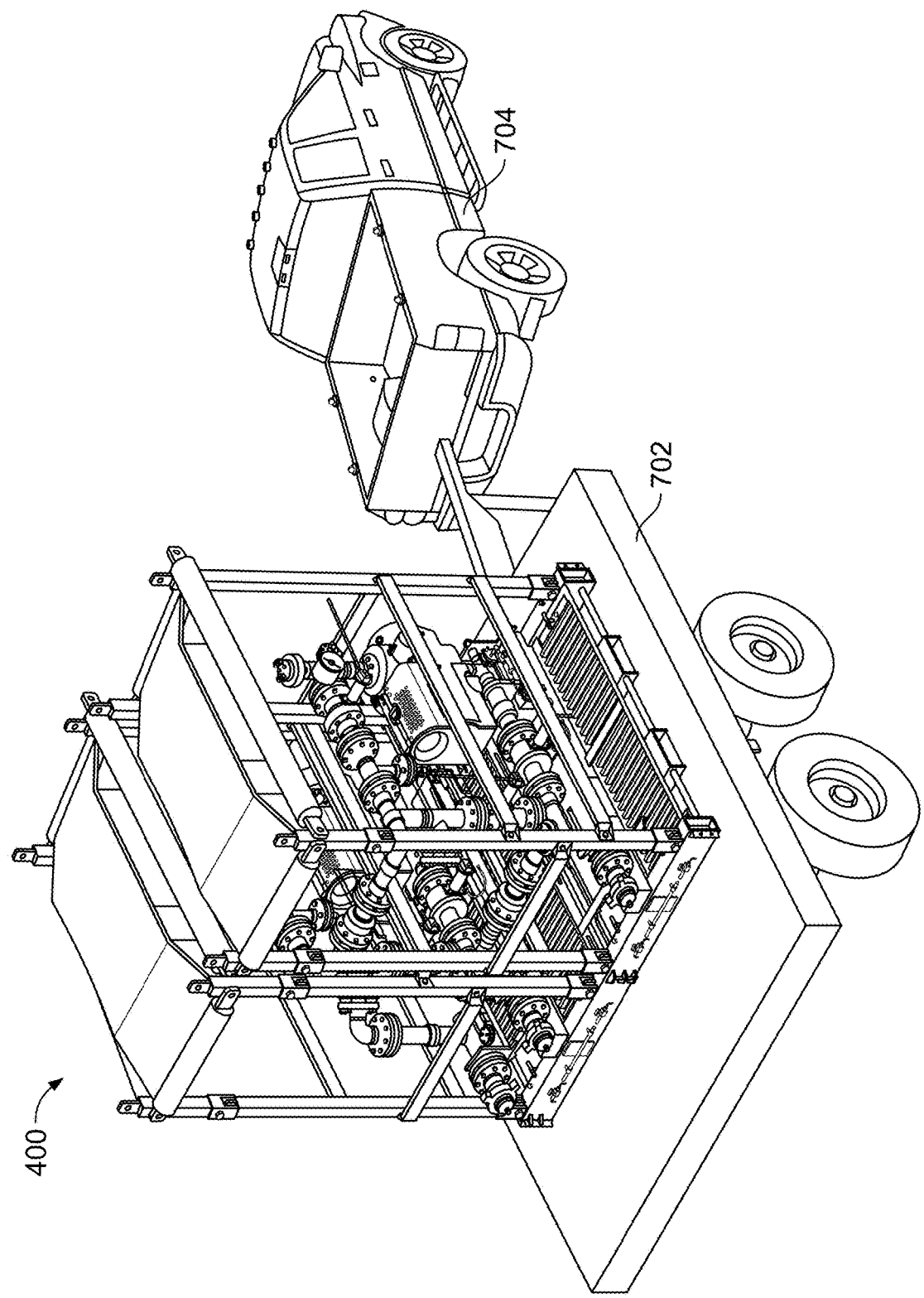
FIG. 7 illustrates the example mobile apparatus of FIG. 4 on a trailer that is being towed by a vehicle.

FIG. 7 illustrates the example apparatus 400 positioned on a trailer 702 that is coupled to a vehicle 704. Thus, using the examples disclosed herein, multiphase flowmeters may be conveniently transported to and from different well sites and/or locations.

Figure 8:
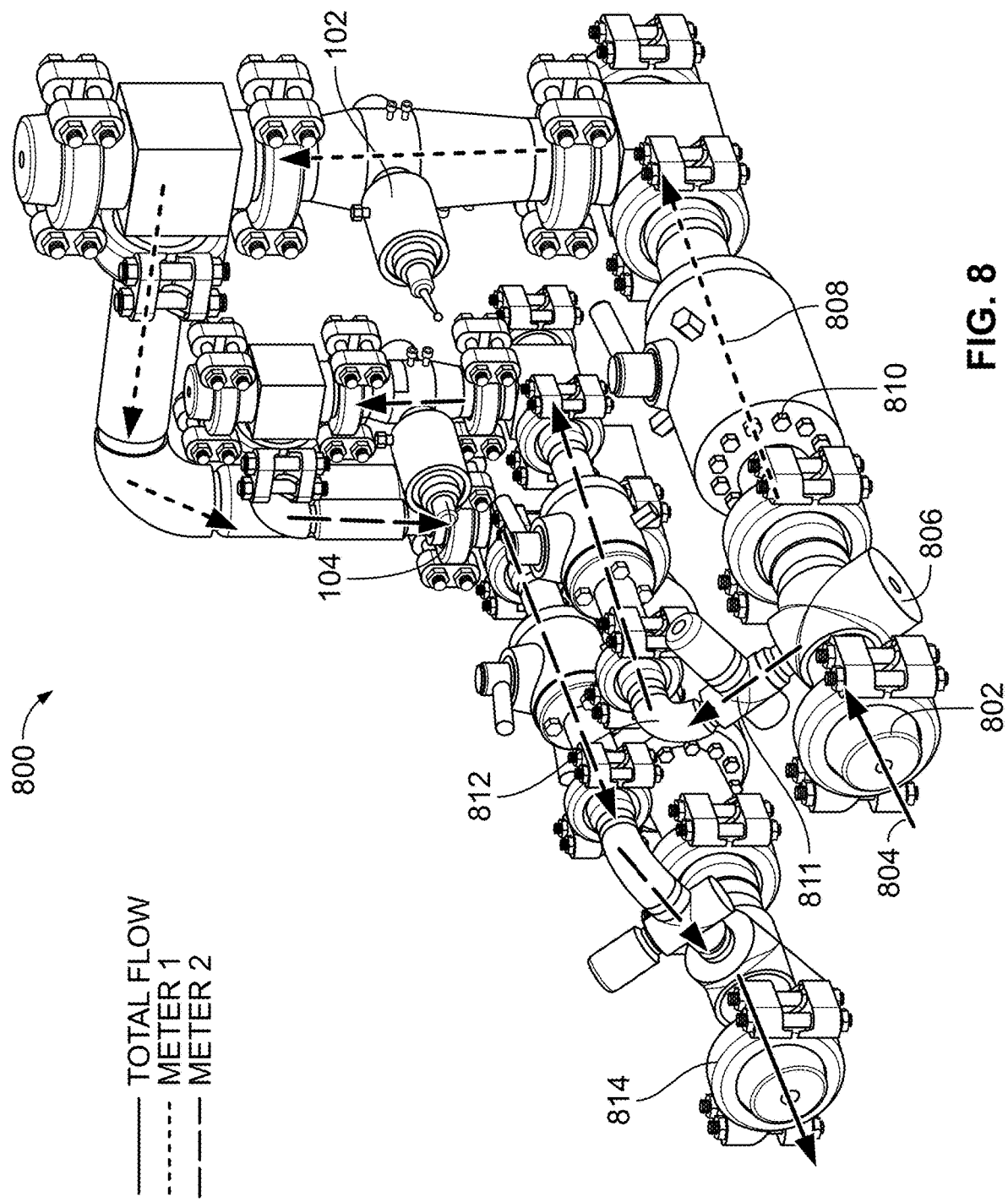
FIG. 8 illustrates another example apparatus including multiphase flowmeters coupled in a fifth asymmetrical flowline arrangement.

FIG. 8 illustrates an example apparatus 800 including the example first multiphase flowmeter 102 and the example second multiphase flowmeter 104 coupled in an asymmetrical flow arrangement in accordance with this disclosure. In operation, multiphase fluid flows into an inlet 802 in a direction generally indicated by arrow 804 toward a manifold 806 that separates the multiphase fluid into a liquid-rich flow in a direction generally indicated by arrow 808 through a first flowline 810 and a gas-rich flow in a direction generally indicated by arrow 811 through a second flowline 812.

In this example, to encourage the liquid-rich flow to flow through the first flowline 810 and to encourage the gas-rich flow to flow through the second flowline 812, the first flowline 810 has a larger and/or different diameter (e.g., a different cross section) than the second flowline 812 and the second flowline 812 has a somewhat vertically positioned portion that extends from and/or relative to the first flowline 810. However, in other examples, the first and/or second flowlines 810, 812 may be differently sized and/or configured. For example, in some examples, the relative angle between the first flowline 810 and the second flowline 812 may be 45-degrees or any other suitable angle. After the fluid flows through the respective first and second multiphase flowmeters 102, 104, the flows are combined at an exit, an exit manifold and/or outlet 814.

FIG. 9 illustrates an example table 900 including results obtained in accordance with the teachings of this disclosure. The table 900 includes a first column 902 identifying different characteristics and/or parameters and a second column 904 including results obtained using a single flowmeter. The table 900 also includes third and fourth columns 906, 908 including results obtained using an example inlet manifold that diverts the fluid into different flow streams having substantially the same gas fractions, oil fractions and water fractions. The table 900 also includes fifth and sixth columns 910, 912 including results obtained using an example inlet manifold that encourages a liquid-rich flow toward the first multiphase flowmeter and a gas-rich flow toward the second multiphase flowmeter. As indicated by comparing the results included in the columns 904-912, results associated with the inlet manifold encouraging asymmetrical phase fractions have a lower combined gas uncertainty (e.g., less error), a lower combined liquid uncertainty (e.g., less error) and a lower combined water liquid ratio uncertainty (e.g., less error).

From the foregoing, it will be appreciated that the example methods, apparatus and articles of manufacture improve the accuracy of the measured and/or determined water liquid ratio by encouraging the separation of flow including a liquid-rich flow and a gas-rich flow. Thus, the examples disclosed herein do not completely separate the phases from one another but instead encourage one of the legs and/or flowlines of an inlet manifold to receive the liquid-rich fluid based on momentum and/or gravity and for the others of the legs and/or flowlines of the inlet manifold to receive the gas-rich fluid based on momentum and/or gravity. By encouraging one of the legs to have the liquid-rich fluid flow, a highly accurate water liquid ratio (WLR) and liquid rate may be determined therefrom as compared to the water liquid ratio and liquid rate determined from fluid flows having a higher gas fraction.

In some examples, an example mobile skid assembly produced in accordance with the teachings of this disclosure includes two or more multiphase flowmeters including flowlines and/or an inlet manifold that encourages the diversion of a multiphase fluid into a liquid-rich fluid directed toward a first multiphase flowmeter(s) and a gas-rich fluid directed toward a second multiphase flowmeter(s). Thus, using examples disclosed herein, multiphase fluids may be separated and thereafter analyzed in parallel (e.g., analyzed at substantially the same time).

After the fluid flows through respective first and second flowmeters, the fluid is recombined at an outlet manifold and/or outlet of the skid assembly. The first multiphase flowmeter(s) may be similar and/or different from the second multiphase flowmeter(s). The first flowline(s) stemming from the inlet manifold may be similar and/or different from the second flowline(s) stemming from the inlet manifold (e.g., a different diameter, a different cross-section, a different length, a different angle and/or pitch relative to the earth's surface, etc.).

An example method includes configuring an inlet manifold, a first flowline, and a second flowline to encourage a first fluid flow through the first flowline having a first gas fraction and a second fluid flow through the second flow line having a second gas fraction, the first gas fraction being less than the second gas fraction; flowing the first fluid flow through the first flowline and flowing the second fluid flow through the second flow line; and determining at least one of 1) a first water liquid ratio of the first fluid flow through the first flowline; 2) a first liquid flow rate of the first fluid flow through the first flow line; or 3) a first gas flow rate of the first fluid flow through the first flow line.

In some examples, the method includes determining at least one of 1) a second water liquid ratio of the second fluid flow through the second flowline; 2) a second liquid flow rate of the second fluid flow through the second flow line; or 3) a second gas flow rate of the second fluid flow through the second flow line. In some examples, the method includes flowing the second fluid flow through the second flow line includes diverting the second fluid flow in a non-horizontal direction via the inlet manifold to enable the second flow to have the second gas fraction. In some examples, flowing the first fluid flow through the first flow line includes flowing the first fluid flow along a first axis of the first flowline, the first axis is substantially coaxial with a second axis of an inlet of the inlet manifold to enable the first gas fraction to be less than the second gas fraction.

An example method includes flowing fluid into an inlet manifold; and diverting the fluid based on a configuration of the inlet manifold between a first fluid flow through a first flowline and a second fluid flow through a second flow line, the first fluid flow having a first phase fraction different than a second phase fraction of the fluid second flow. In some examples, the method includes 1) determining a first water liquid ratio of the first fluid flow through the first flowline; and 2) determining a second water liquid ratio of the second flow through the second flowline, the first water liquid ratio having a higher accuracy than the second water liquid ratio based on a first gas fraction of the first phase fraction being less than a second gas fraction of the second phase fraction.

An example apparatus includes an inlet manifold; an outlet; and first and second flowlines coupled between the inlet manifold and the outlet, when the inlet manifold receives a multiphase fluid, the inlet manifold encourages the flow of a first multiphase fluid having a first gas fraction through the first flowline and encourages the flow of a second multiphase fluid having a second gas fraction through the second flowline, the first gas fraction is less than the second gas fraction. In some examples, when the inlet manifold receives the multiphase fluid, the inlet manifold encourages the flow of the first multiphase fluid having a first liquid fraction through the first flowline and encourages the flow of the second multiphase fluid having a second liquid fraction through the second flowline, the first liquid fraction is greater than the second liquid fraction. In some examples, the first flowline is vertically displaced from the second flowline to encourage the flow of the first multiphase fluid having the first liquid fraction to flow through the first flowline and to encourage the flow of the second multiphase fluid having the second gas fraction to flow through the second flowline.

In some examples, the apparatus includes a first multiphase flow meter coupled to the first flowline and a second multiphase flowmeter coupled to the second flowline, the first multiphase flowmeter to determine at least one of a first water liquid ratio of the first multiphase fluid flowing through the first flowline, a first liquid flow rate of the first multiphase fluid flowing through the first flowline, and a first gas flow rate of the first multiphase fluid flowing through the first flowline, the second multiphase flowmeter to determine at least one of a second water liquid ratio of the second multiphase fluid flowing through the second flowline, a second liquid flow rate of the second multiphase fluid flowing through the second flowline, and a second gas flow rate of the second multiphase fluid flowing through the second flowline, an accuracy of the first water liquid ratio being greater than an accuracy of the second water liquid ratio, an accuracy of the first liquid flow rate being greater than an accuracy of the second liquid flow rate. In some examples, the first flowline has a larger cross-section than the second the second flowline. In some examples, the first flowline is coaxially positioned relative to an inlet of the inlet manifold to encourage the flow of the first multiphase fluid having the first gas fraction through the first flowline.

In some examples, a first axis of the second flowline is offset relative to a second axis of an inlet of the inlet manifold to encourage the flow of the second multiphase fluid having the second gas fraction through the second flowline. In some examples, the inlet manifold is to encourage the flow of the first multiphase fluid having the first gas fraction through the first flowline based at least in part on the positioning of an inlet of the inlet manifold relative to the first flowline and a momentum of the different components the multiphase fluid at an intersection between the first and second flowlines. In some examples, the inlet manifold is to encourage the flow of the second multiphase fluid having the second gas fraction through the second flowline based at least in part on the relative position of an inlet of the inlet manifold relative to the second flowline. In some examples, the inlet manifold does not include a separator therein to encourage the flow of the first multiphase fluid having the first gas fraction to the first flowline and to encourage the second multiphase fluid having the second gas fraction through the second flowline. In some examples, the apparatus includes a skid onto which the inlet manifold, the outlet manifold, and the first and second flowlines are disposed to enable mobility of the apparatus. In some examples, one or more of the first flowline or the second flowline has an axis disposed at a non-horizontal angle to encourage the flow of the multiphase fluid having the first gas fraction to the first flowline and to encourage the flow of the second multiphase fluid having the second gas fraction to the second flowline.

An example apparatus includes an inlet manifold; first and second flowlines coupled to the inlet manifold; means for encouraging fluid flowing through the inlet manifold to be diverted between a first multiphase fluid flowing through the first flowline and a second multiphase fluid flowing through the second flowline, where the first multiphase fluid flow has a greater gas fraction than the second multiphase fluid flow and the second multiphase fluid flow has a greater liquid fraction than the first multiphase fluid flow. In some examples, the second flowline is vertically displaced relative to the first flowline to enable the first multiphase fluid to have a greater gas fraction than the second multiphase fluid.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

The invention claimed is:

1. A method, comprising:
    flowing fluid into an inlet manifold;
    diverting the fluid based on a configuration of the inlet manifold between a first fluid flow through a first flowline and a second fluid flow through a second flow line, the first fluid flow having a first phase fraction different than a second phase fraction of the fluid second flow,
    determining a first water liquid ratio of the first fluid flow through the first flowline; and
    determining a second water liquid ratio of the second flow through the second flowline, the first water liquid ratio having a higher accuracy than the second water liquid ratio based on a first gas fraction of the first phase fraction being less than a second gas fraction of the second phase fraction.

2. The method of claim 1, wherein diverting the fluid based on the configuration of the inlet manifold between the first fluid flow through the first flowline and the second fluid flow through the second flow line includes diverting the second fluid flow in a non-horizontal direction via the inlet manifold to enable the second flow to have the second phase fraction.

3. The method of claim 1, wherein the first flowline has a larger cross-section than the second the second flowline.

4. An apparatus, comprising:
    an inlet manifold;
    an outlet;
    first and second flowlines coupled between the inlet manifold and the outlet, when the inlet manifold receives a multiphase fluid, the inlet manifold causes the flow of a first multiphase fluid having a first gas fraction through the first flowline and causes the flow of a second multiphase fluid having a second gas fraction through the second flowline, the first gas fraction is less than the second gas fraction; and
    a first multiphase flow meter coupled to the first flowline and a second multiphase flowmeter coupled to the second flowline, the first multiphase flowmeter to determine at least one of a first water liquid ratio of the first multiphase fluid flowing through the first flowline and a first liquid flow rate of the first multiphase fluid flowing through the first flowline, the second multiphase flowmeter to determine at least one of a second water liquid ratio of the second multiphase fluid flowing through the second flowline and a second liquid flow rate of the second multiphase fluid flowing through the second flowline, an accuracy of the first water liquid ratio being greater than an accuracy of the second water liquid ratio when both first and second multiphase flow meters determine the first and second water liquid ratios, an accuracy of the first liquid flow rate being greater than an accuracy of the second liquid flow rate when both first and second multiphase flow meters determine the first and second liquid flow rates.

5. The apparatus of claim 4, wherein, when the inlet manifold receives the multiphase fluid, the inlet manifold causes the flow of the first multiphase fluid having a first liquid fraction through the first flowline and causes the flow of the second multiphase fluid having a second liquid fraction through the second flowline, the first liquid fraction is greater than the second liquid fraction.

6. The apparatus of claim 4, wherein the first flowline is vertically displaced from the second flowline to cause the flow of the first multiphase fluid having the first liquid fraction to flow through the first flowline and to cause the flow of the second multiphase fluid having the second gas fraction to flow through the second flowline.

7. The apparatus of claim 4, further including the first multiphase flowmeter to determine a first gas flow rate of the first multiphase fluid flowing through the first flowline and the second multiphase flowmeter to determine a second gas flow rate of the second multiphase fluid flowing through the second flowline.

8. The apparatus of claim 4, wherein the first flowline has a larger cross-section than the second the second flowline.

9. The apparatus of claim 4, wherein the first flowline is coaxially positioned relative to an inlet of the inlet manifold to cause the flow of the first multiphase fluid having the first gas fraction through the first flowline.

10. The apparatus of claim 4, wherein a first axis of the second flowline is offset relative to a second axis of an inlet of the inlet manifold to cause the flow of the second multiphase fluid having the second gas fraction through the second flowline.

11. The apparatus of claim 4, wherein the inlet manifold is to cause the flow of the first multiphase fluid having the first gas fraction through the first flowline based at least in part on the positioning of an inlet of the inlet manifold relative to the first flowline and a momentum of the different components of the multiphase fluid at an intersection between the first and second flowlines.

12. The apparatus of claim 4, wherein the inlet manifold is to cause the flow of the second multiphase fluid having the second gas fraction through the second flowline based at least in part on the relative position of an inlet of the inlet manifold relative to the second flowline.

13. The apparatus of claim 4, wherein the inlet manifold does not include a separator therein to cause the flow of the first multiphase fluid having the first gas fraction to the first flowline and to cause the second multiphase fluid having the second gas fraction through the second flowline.

14. The apparatus of claim 4, further including a skid onto which the inlet manifold, the outlet manifold, and the first and second flowlines are disposed to enable mobility of the apparatus.

15. The apparatus of claim 4, wherein one or more of the first flowline or the second flowline has an axis disposed at a non-horizontal angle to cause the flow of the multiphase fluid having the first gas fraction to the first flowline and to cause the flow of the second multiphase fluid having the second gas fraction to the second flowline.

\* \* \* \* \*